(12) United States Patent
Li et al.

(10) Patent No.: US 6,385,277 B1
(45) Date of Patent: May 7, 2002

(54) METHODS AND APPARATUS FOR USING INTERLACED SCANS IN CT IMAGING

(75) Inventors: Jianying Li, New Berlin; Robert F. Senzig, Germantown, both of WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/475,590

(22) Filed: Dec. 30, 1999

(51) Int. Cl.[7] .......................... A61B 6/00; G01N 23/00; G21K 1/12; H05G 1/60

(52) U.S. Cl. ................................. 378/4; 378/9

(58) Field of Search .......................... 378/4, 9

(56) References Cited

U.S. PATENT DOCUMENTS 5,265,142 A * 11/1993 Hsieh ........................... 378/4

* cited by examiner

Primary Examiner—Robert H. Kim
Assistant Examiner—Courtney Thomas
(74) Attorney, Agent, or Firm—Carl B. Horton, Esq.; Armstrong Teasdale LLP

(57) ABSTRACT

In one embodiment of the present invention, a method for collecting views for imaging an object utilizing a CT imaging system is provided. The method includes steps of: performing a first rotational scan of an object to acquire a first set of views of the object; performing a second rotational scan of the object to acquire a second set of views of the object; offsetting starting angular views of the second rotational scan relative to the first rotational scan so that the first set of views and the second set of views form a set of interlaced views; and reconstructing an image of the object utilizing the first set of views and the second set of views.

14 Claims, 4 Drawing Sheets

METHODS AND APPARATUS FOR USING INTERLACED SCANS IN CT IMAGING

BACKGROUND OF THE INVENTION

This invention relates generally to computed tomographic (CT) imaging, and more particularly to methods and apparatus for boosting image resolution for relatively long duration scans.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In known CT systems, multiple-sec scans are used to increase signal strength in certain calibration and patient scans, and to increase angular sampling. For example, one known scanner offers 2-sec, 3-sec, and 4-sec scan speeds in addition to the more commonly used 0.8-sec and 1-sec scan speeds. For a 2-sec scan speed, a gantry of the scanner rotates 360 degrees in 2 seconds, collecting 984×2=1968 angular views. The view-to-view angular interval is 0.18 degree. Views are combined before reconstruction to increase reconstruction speed Combining the views reduces angular sampling, which is disadvantageous in some cases.

If a view uncompressed reconstruction were used, the reconstruction kernel could be boosted to increase image resolution without increasing aliasing artifacts. Increased resolution without increased aliasing would be advantageous for imaging the head and spines. However, because of the slower rotation speed in multiple-sec scans, multiple-sec scans produce more focal spot movement than 0.8 and 1-sec scans. The performance on axial encoding accuracy is also better with 0.8 and 1-sec scans than with 2- and 4-sec scans.

It would therefore be desirable to provide methods and apparatus to provide multiple-sec scans suitable for use with view uncompressed reconstruction.

BRIEF SUMMARY OF THE INVENTION

There is therefore provided, in one embodiment of the present invention, a method for collecting views for imaging an object utilizing a CT imaging system. The method includes steps of: performing a first rotational scan of an object to acquire a first set of views of the object; performing a second rotational scan of the object to acquire a second set of views of the object; offsetting starting angular views of the second rotational scan relative to the first rotational scan so th at the first set of views and the second set of views form a set of interlaced views; and reconstructing an image of the object utilizing the first set of views and the second set of views.

The above described embodiment provides shorter interlaced scans that reduce focal spot movement and encoding accuracy problems associated with slower scan speeds, while still providing increased image resolution by using kernel boosting without increasing aliasing artifacts.

DETAILED DESCRIPTION OF THE INVENTION

Figure 1:
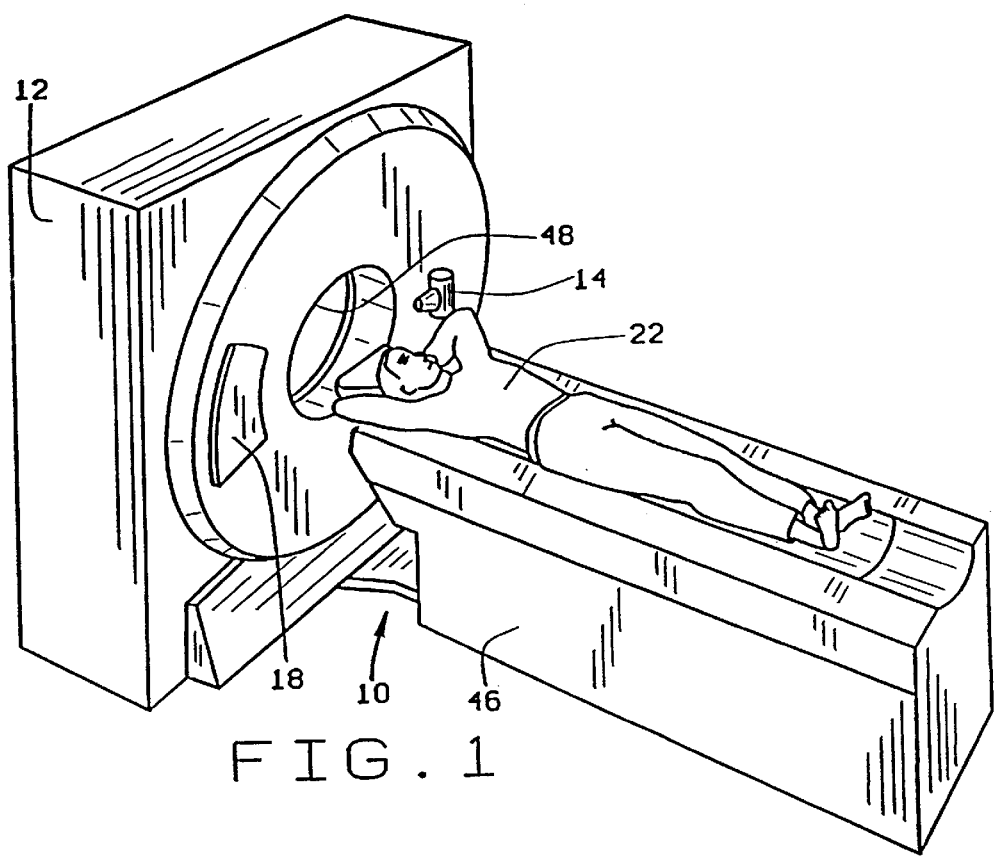
FIG. 1 is a pictorial view of a CT imaging system.
Figure 2:
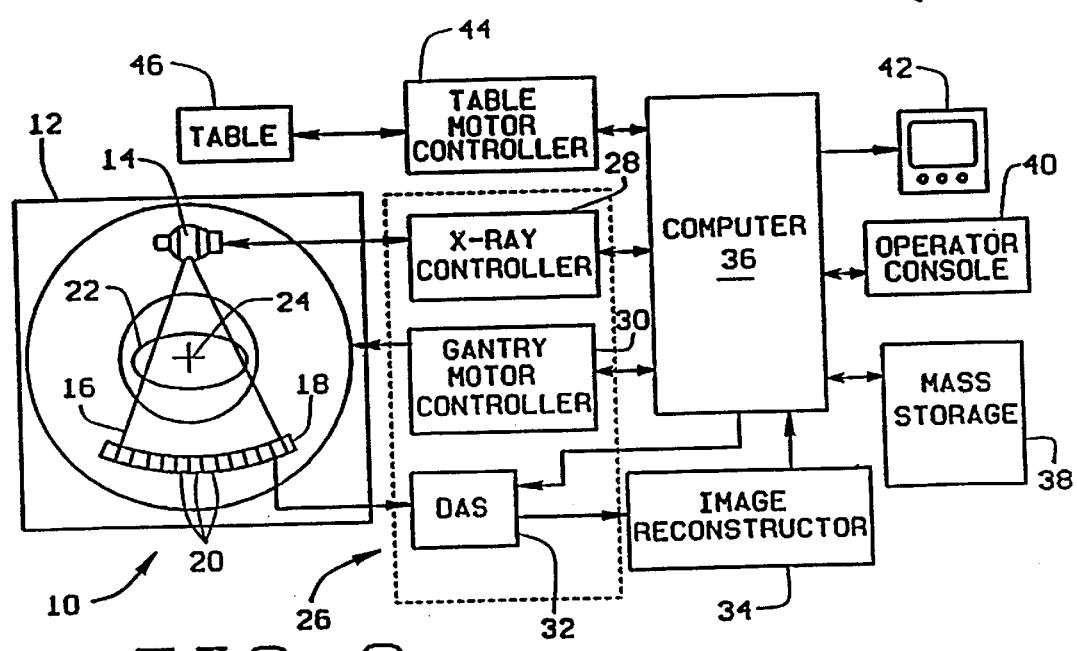
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment of the present invention, multiple interlaced scans performed by CT imaging system 10 replace multiple-sec scans to permit view uncompressed reconstruction to further boost the image resolution. For example, in place of a 2-sec scan, two 1-sec scans are performed. At a trigger frequency of 984/second, a starting angular view of the second 1-sec scan will have a displacement of 0.18 degree from the starting angular view of the first 1-sec scan. The scan data of these two 1-sec scans, in one embodiment, are added together in the conventional way to reduce noise. In another embodiment, the scan data of the 1-sec scans are combined (sorted) to form 1968 views to provide better image resolution. In another embodiment, CT imaging system 10 selectively provides a conventional addition of scan data and a sorting of scan data, depending upon a selection input by an operator.

In one embodiment, CT imaging system 10 monitors patient motion by comparing corresponding views at different time(s) of the scan. This information is then used to provide a correction for patient motion for image reconstruction. CT imaging system 10 also analyzes information obtained during the first scan to determine an optimal current to supply to radiation source 14 (for example, an x-ray generating tube) to optimize signal output by detector array 18.

Embodiments of the present invention have been tested with diagnostic data collection mode using a CT Performance Phantom (GE Medical Systems, Waukesha, Wis.). Scans were obtained on the wire section of the phantom. The scans were a 2-sec scan, a 1-sec scan with starting angle at 0 degree, and a 1-sec scan with starting angle at 0.18 degrees. Images were obtained with two different high resolution filter kernels (Kernel 1 and Kernel 2) using the view-uncompressed reconstruction from the 2-sec scans and from interlacing the two 1-sec scans to compare image resolutions. Images were also obtained with a kernel boosted high-resolution filter kernel using view-uncompressed and view-compressed reconstruction from the 2-sec scans, as well as from the two interlaced 1-sec scans to compare aliasing artifact content. Tables 1 and 2 below show the resolution comparison with the phantom centered and 60 mm off-centered, respectively, which indicate that practically there is no difference between the 2-sec scan and interlaced 1-sec scan images.

TABLE 1

IMAGE RESOLUTION COMPARISON WITH PHANTOM CENTERED

| Scan | MTF (StDv) (Kernel 1) | | MTF (StDv) (Kernel 2) | |
|---|---|---|---|---|
| | 50% | 10% | 50% | 10% |
| 2-sec | 8.43 (0.11) | 11.81 (0.06) | 10.59 (0.12) | 13.98 (0.07) |
| Interlaced 1-sec | 8.48 (0.10) | 11.86 (0.05) | 10.74 (0.12) | 14.01 (0.10) |

TABLE 2

IMAGE RESOLUTION COMPARISON WITH PHANTOM OFF-CENTERED BY 60 mm

| Scan | MTF (StDv) (STAND) | | MTF (StDv) (Kernel 1) | |
|---|---|---|---|---|
| | 50% | 10% | 50% | 10% |
| 2-sec | 3.87 (0.11) | 6.72 (0.06) | 6.93 (0.12) | 10.90 (0.07) |
| Interlaced 1-sec | 3.82 (0.10) | 6.73 (0.05) | 7.02 (0.12) | 10.99 (0.10) |

Figure 3:
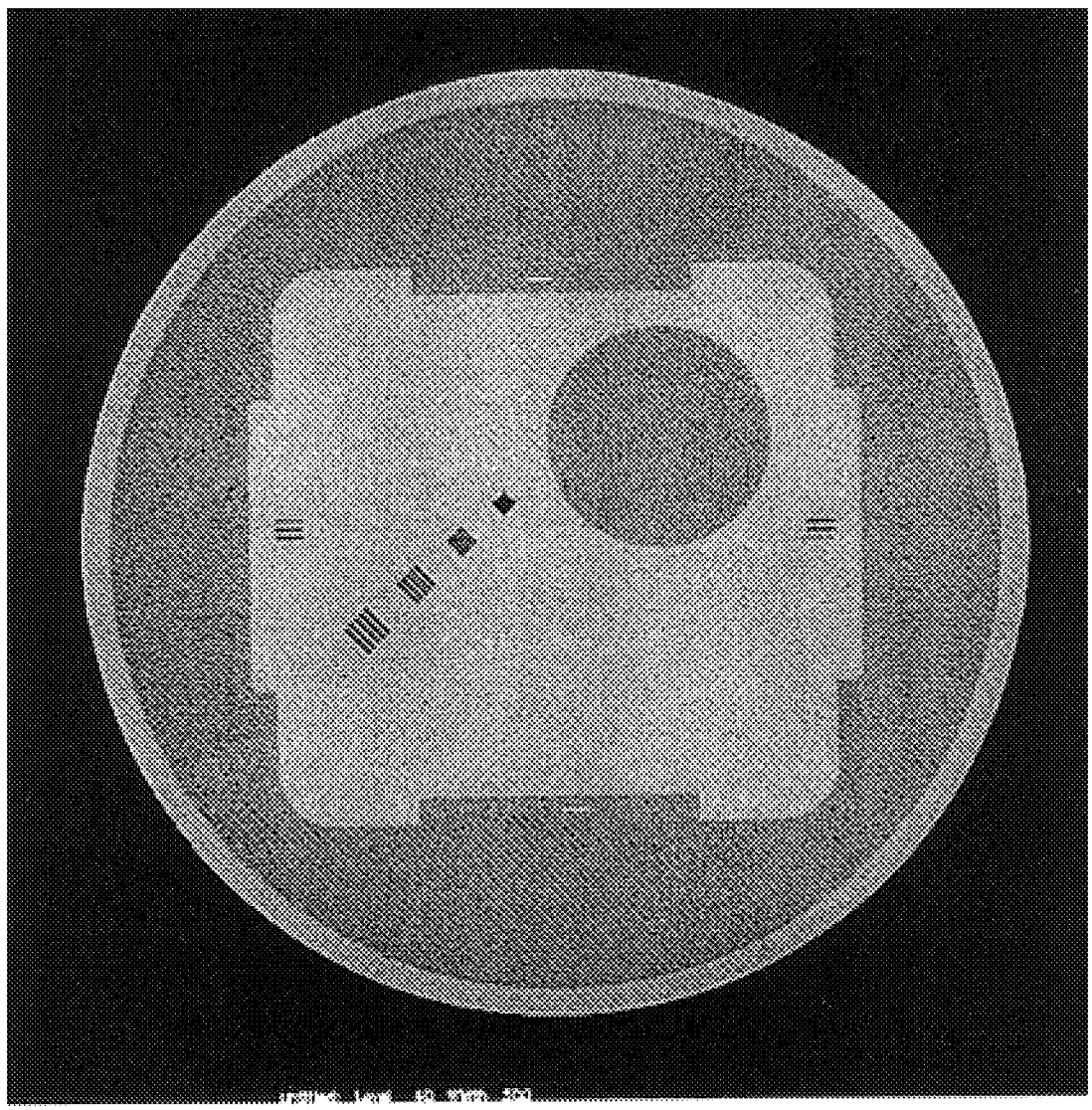
FIG. 3 is a view-uncompressed reconstruction image of a phantom from a 2-sec scan.
Figure 4:
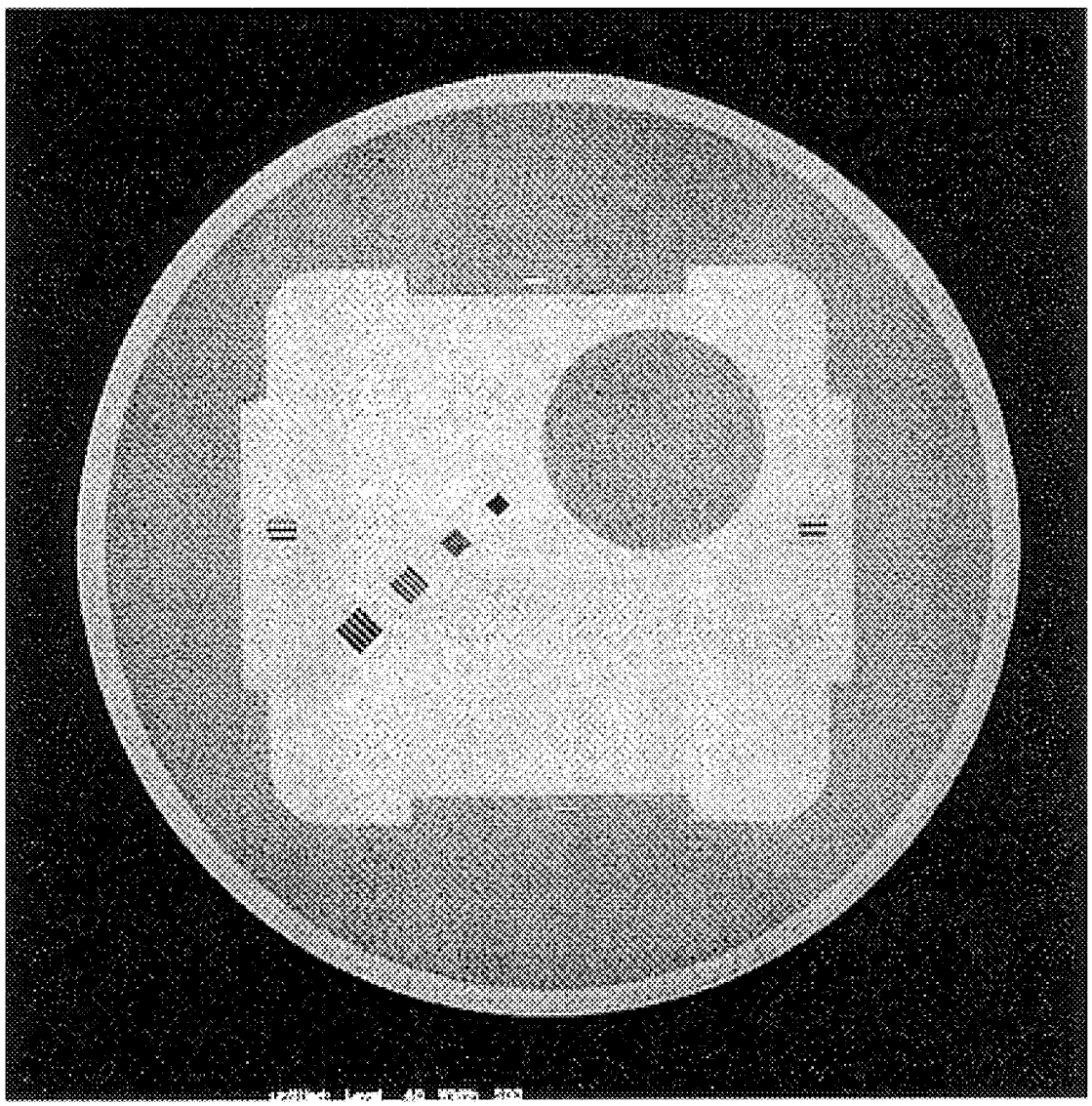
FIG. 4 is an image of the phantom of FIG. 3 reconstructed from two 1-sec scans in which a starting angle of the second 1-sec scan was shifted 0.18 degree so that the first and second scans were interlaced.
Figure 5:
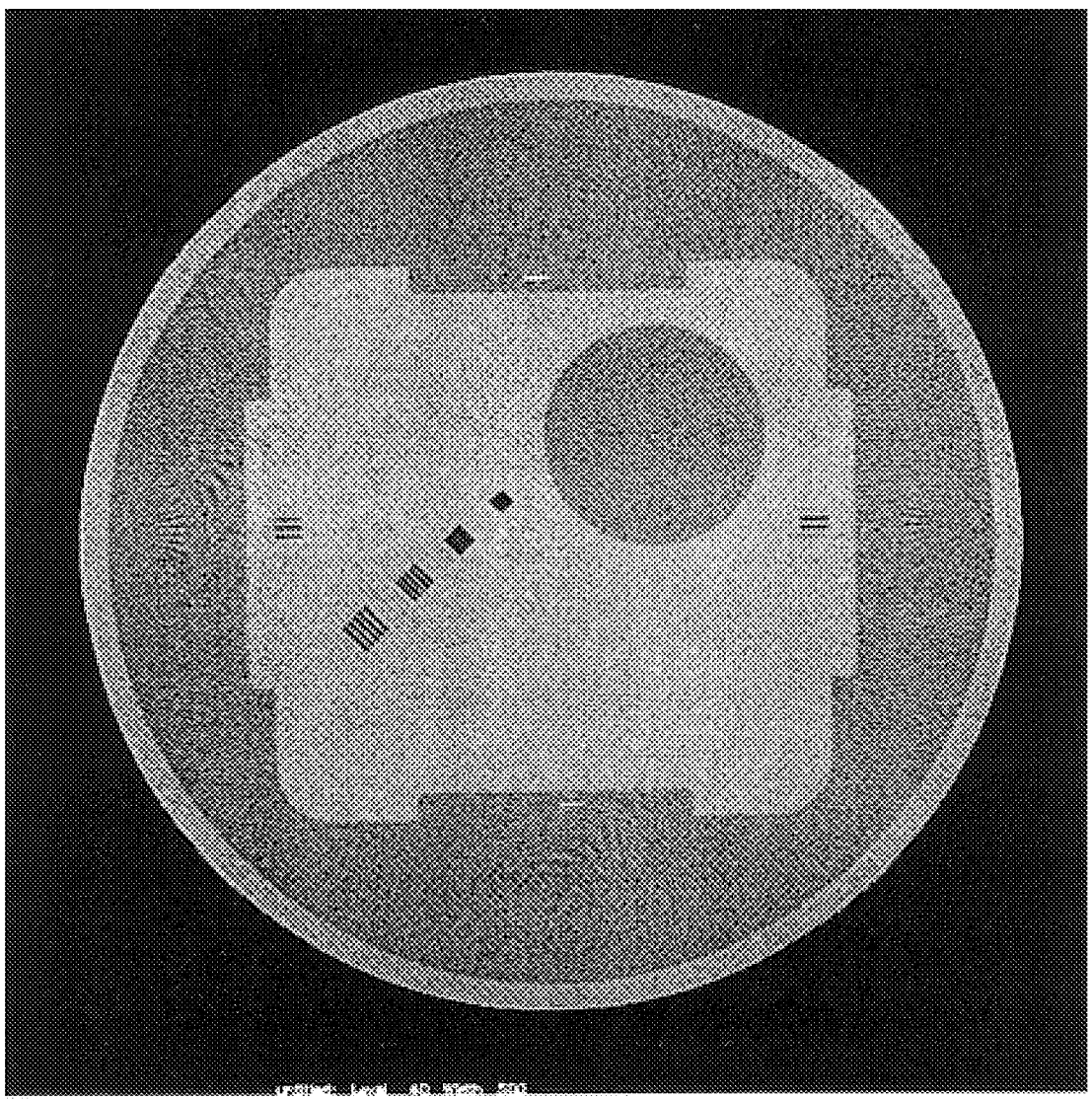
FIG. 5 is a view-compressed reconstruction image of the phantom of FIG. 3 from a 2-sec scan, showing increased aliasing relative to the images of FIGS. 3 and 4.

FIGS. 3, 4, and 5 show the image aliasing artifacts comparison with the kernel boosted high-resolution algorithm. FIG. 3 shows a view-uncompressed reconstruction image from the 2-sec scan. FIG. 4 shows an image with two 1-sec scans in which the starting angle of the second 1-sec scan is shifted 0.18 degree to provide interlacing with respect to the first 1-sec scan. FIG. 5 shows a view-compressed reconstruction image from a 2-sec scan. While the view-uncompressed reconstruction from the 2-sec scan and from the interlaced 1-sec scans in FIGS. 3 and 4, respectively, demonstrated similar image quality and artifacts content, the view compressed reconstruction from the 2-sec scan data in FIG. 5 showed much increased aliasing artifact. Thus, by using two interlaced shorter scans, the present invention effectively controls image aliasing artifacts.

From the preceding description of various embodiments of the present invention, it is evident that the use of shorter-interlaced-scans reduces focal spot movement and encoding accuracy problems associated with slower scan speeds. At the same time, image resolution can be increased with kernel boosting, without increasing aliasing artifacts. As an additional advantage, patient information acquired from the first scan can be used to adjust the tube current to optimize the output signal.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required. Accordingly, the spirit and scope of the invention are to be limited only by the terms of the appended claims and legal equivalents.

What is claimed is:

1. A method for collecting views for imaging an object utilizing a computed tomographic (CT) imaging system, said method comprising:

performing a first rotational scan of an object to acquire a first set of views of the object;

performing a second rotational scan of the object to acquire a second set of views of the object;

offsetting starting angular views of the second rotational scan relative to the first rotational scan so that the first set of views and the second set of views form a set of interlaced views; and comparing views from the first set of views with views from the second set of views to detect patient motion, and correcting for the detected patient motion.

2. A method for collecting views for imaging an object utilizing a computed tomographic (CT) imaging system, said method comprising:

performing a first rotational scan of an object to acquire a first set of views of the object;

analyzing the first set of views, and adjusting a current supplied to the radiation source for acquiring the second set of views in accordance with results of the analysis of the first set of views;

performing a second rotational scan of the object to acquire a second set of views of the object;

offsetting starting angular views of the second rotational scan relative to the first rotational scan so that the first set of views and the second set of views form a set of interlaced views; and reconstructing an image of the object utilizing the first set of views and the second set of views.

3. A method in accordance with claim 1 wherein the first rotational scan and the second rotational scan are performed in no more than one second each.

4. A method in accordance with claim 2 and further comprising performing additional rotational scans to acquire additional sets of views, and offsetting starting views of the additional rotational scans so that the first, the second, and the additional sets of views are offset from one another, and wherein reconstructing an image of the object comprises reconstructing an image of the object utilizing the first, the second, and the additional sets of views.

5. A method in accordance with claim 1 wherein the first set of views and the second set of views each comprise 984 angular views.

6. A method in accordance with claim 2 wherein reconstructing an image of the object comprises performing view uncompressed reconstruction.

7. A method in accordance with claim 2 wherein offsetting starting angular views of the second rotational scan relative to the first rotational scan comprises starting the second rotational scan so that a starting angular view of the second set of views is offset 0.18 degree from a starting angular view of the first set of views.

8. A computed tomographic (CT) imaging system for imaging an object, said imaging system being configured to:

perform a first rotational scan of an object to acquire a first set of views of the object;

perform a second rotational scan of the object to acquire a second set of views of the object;

offset starting angular views of the second rotational scan relative to the first rotational scan so that the first set of views and the second set of views form a set of interlaced views; and compare views from the first set of views with views from the second set of views to detect patient motion, and to correct for the detected patient motion.

9. A computed tomographic (CT) imaging system for imaging an object, said imaging system being configured to:

perform a first rotational scan of an object to acquire a first set of views of the object;

analyze the first set of views, and adjust a current supplied to the radiation source for acquiring the second set of views in accordance with results of the analysis of the first set of views;

perform a second rotational scan of the object to acquire a second set of views of the object;

offset starting angular views of the second rotational scan relative to the first rotational scan so that the first set of views and the second set of views form a set of interlaced views; and reconstruct an image of the object utilizing the first set of views and the second set of views.

10. A CT imaging system in accordance with claim 8 further configured to provide a scanning rate sufficient to perform the first rotational scan and the second rotational scan in no more than one second each.

11. A CT imaging system in accordance with claim 9 and further configured to perform additional rotational scans to acquire additional sets of views, and to offset starting views of the additional rotational scans so that the first, the second, and the additional sets of views are offset from one another, and wherein said system being configured to reconstruct an image of the object comprises said system being configured to reconstruct an image of the object utilizing the first, the second, and the additional sets of views.

12. A CT imaging system in accordance with claim 8 wherein the first set of views and the second set of views each comprise 984 angular views.

13. A CT imaging system in accordance with claim 9 wherein said system being configured to reconstruct an image of the object comprises said system being configured to perform view uncompressed reconstruction.

14. A CT imaging system method in accordance with claim 8 wherein said system being configured to offset starting angular views of the second rotational scan relative to the first rotational scan comprises said system being configured to start the second rotational scan so that a starting angular view of the second set of views is offset 0.18 degree from a starting angular view of the first set of views.

* * * * *